US011549120B2

(12) United States Patent
Kato et al.

(10) Patent No.: US 11,549,120 B2
(45) Date of Patent: Jan. 10, 2023

(54) METHOD FOR INTRODUCING SUBSTANCE INTO PLANT

(71) Applicants: JAPAN TOBACCO INC., Tokyo (JP); TOKYO METROPOLITAN UNIVERSITY, Tokyo (JP); RIKEN, Wako (JP)

(72) Inventors: Norio Kato, Shizuoka (JP); Takashi Okamoto, Tokyo (JP); Takatoshi Kiba, Saitama (JP); Erika Toda, Saitama (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 16/089,813

(22) PCT Filed: Mar. 28, 2017

(86) PCT No.: PCT/JP2017/013868
§ 371 (c)(1),
(2) Date: Sep. 28, 2018

(87) PCT Pub. No.: WO2017/171092
PCT Pub. Date: Oct. 5, 2017

(65) Prior Publication Data
US 2020/0123553 A1   Apr. 23, 2020

(30) Foreign Application Priority Data
Mar. 31, 2016 (JP) .............................. JP2016-070288

(51) Int. Cl.
C12N 15/82 (2006.01)
A01H 6/46 (2018.01)
A01H 1/00 (2006.01)
C12N 9/42 (2006.01)

(52) U.S. Cl.
CPC ........... *C12N 15/8206* (2013.01); *A01H 1/00* (2013.01); *A01H 6/4684* (2018.05); *C12N 9/2437* (2013.01); *C12Y 302/01015* (2013.01)

(58) Field of Classification Search
CPC .................................................. C12N 15/8206
See application file for complete search history.

(56) References Cited

U.S. PATENT DOCUMENTS

2011/0321192 A1   12/2011   Van Kan et al.
2012/0016144 A1   1/2012    Petrie et al.

FOREIGN PATENT DOCUMENTS

JP    2012-509059 A      4/2012
RU    2 403 709 C2      11/2008

OTHER PUBLICATIONS

Zaghmout, O. Theoretical and Applied Genetics 89: 577-582 (1994).*
Lazzeri et al. Theoretical and Applied Genetics 81: 437-444 (1991).*
Wei et al. Biotechnology Letters 23: 799-803 (2001).*
Krautwig et al. Plant Cell, Tissue and Organ Culture 39: 43-48 (1994).*
Gronwald et al. Plant Physiology 70: 1391-1395 (1982).*
Moore, M. (2008) http://farmindustrynews.com/print/corn-hybrids/shallow-gene-pool (pp. 1-3).*
Zaghmout et al. Theoretical and Applied Genetics 86: 721-730 (1993).*
Zaghmout, O. Theoretical and Applied Genetics 89: 577-582 (1994) (Year: 1994).*
Lazzeri et al. Theoretical and Applied Genetics 81: 437-444 (1991) (Year: 1991)*
Wei et al. Biotechnology Letters 23: 799-803 (2001) (Year: 2001).*
Krautwig et al. Plant Cell, Tissue and Organ Culture 39: 43-48 (1994) (Year: 1994).*
Gronwald et al. Plant Physiology 70: 1391-1395 (1982) (Year: 1982).*
Moore, M. (2008) http://farmindustrynews.com/print/corn-hybrids/shallow-gene-pool (pp. 1-3) (Year: 2008).*
Zaghmout et al. Theoretical and Applied Genetics 86: 721-730 (1993) (Year: 1993).*
Abiko et al., "Gene Expression Profiles in Rice Gametes and Zygotes: Identification of Gamete-Enriched Genes and up- or down-Regulated Genes in Zygotes After Fertilization", Journal of Experimental Botany, vol. 64, No. 7, 2013, pp. 1927-1940.

(Continued)

*Primary Examiner* — David H Kruse
(74) *Attorney, Agent, or Firm* — Birch, Stewart, Kolasch & Birch, LLP

(57) ABSTRACT

The present invention relates to a method for introducing a substance into a plant. The method of the present invention comprises the steps of: obtaining an enzymatically treated and isolated fertilized egg cell by (1-i) isolating a fertilized egg cell from a plant tissue containing a fertilized egg cell, and then treating the fertilized egg cell with an enzyme solution containing a plant tissue-degrading enzyme under a low-titer condition, (1-ii) treating a plant tissue containing a fertilized egg cell with an enzyme solution containing a plant tissue-degrading enzyme under a low-titer condition, and then isolating the fertilized egg cell that has been enzymatically treated, (1-iii) treating a plant tissue containing a fertilized egg cell with an enzyme solution containing a plant tissue-degrading enzyme under a low-titer condition, and simultaneously isolating the fertilized egg cell that has been enzymatically treated, (1-iv) isolating an egg cell and a sperm cell from a plant to produce a fertilized egg by fusing the cells, and then treating the fertilized egg cell with an enzyme solution containing a plant tissue-degrading enzyme under a low-titer condition, or (1-v) treating a plant tissue containing an egg cell with an enzyme solution containing a plant tissue-degrading enzyme under a low-titer condition, and then isolating the egg cell that has been enzymatically treated, and further fusing the egg cell with an isolated sperm cell; and (2) introducing a substance selected from the group consisting of nucleic acids, proteins, and peptides into the resultant enzymatically treated and isolated fertilized egg cell.

13 Claims, 5 Drawing Sheets
(5 of 5 Drawing Sheet(s) Filed in Color)

(56) References Cited

OTHER PUBLICATIONS

Chen et al., "Isolation of egg cells and zygotes of *Torenia foumieri* L. and determination of their surface charge", Zygote, vol. 16, 2008, pp. 179-186.

Chen et al., "Maize (*Zea mays* L.) transformation by Agrobacterium tumefaciens infection of pollinated ovules", Journal of Biotechnology, vol. 171, 2014, pp. 8-16.

Chu et al., "Establishment of an Efficient Medium for Anther Culture of Rice Through Comparative Experiments on the Nitrogen Sources", Scientia Sinica, vol. 18, No. 5, 1975, pp. 659-668, 11 pages total.

Extended European Search Report dated Sep. 12, 2019, for European Application No. 17775623.6.

Furuta et al., "Establishment of a microinjection with isolated rice egg cells and zygotes", Regulation of Plant Growth and Development, vol. 49, p. 100, 2014, 3 pages total, English abstract only.

Gamborg et al., "Nutrient Requirements of Suspension Cultures of Soybean Root Cells", Experimental Cell Research, vol. 50, 1968, pp. 151-158.

He et al., "Regeneration of fertile plants from isolated tobacco zygotes by in vitro culture", Chinese Science Bulletin, vol. 49, No. 8, 2004, pp. 810-814.

Holm et al., "Regeneration of Fertile Barley Plants from Mechanically Isolated Protoplasts of the Fertilized Egg Cell", The Plant Cell, vol. 6, Apr. 1994, pp. 531-543.

Holm et al., "Transformation of barley by microinjection into isolated zygote protoplasts", Transgenic Research, vol. 9, 2000, pp. 21-32.

Holme et al., "Transformation of barley (*Hordeurn vuigare* L.) by Agrobacterium tumefaciens infection of in vitro cultured ovules", Plant Cell Rep., vol. 25, No. 12, 2006, pp. 1325-1335.

Ishii, "Enzymatic Maceration of Plant Tissues by Endo-Pectin Lyase and Endo-Polygalacturonase from Aspergillus japonicus". Physiology and Biochemistry, vol. 66, 1976, pp. 281-289.

Kranz et al., "In vitro fertilization of single, isolated gametes of maize mediated by electrofusion", Sexual Plant Reproduction, vol. 4, 1991, pp. 12-16.

Kranz et al., "In Vitro Fertilization with Isolated Gametes of Maize and Its Application to Study Fertilization Processes and Early Events of Zygote Development", Pollen Angiosperm, Ovules, Springer New York, New York, 1992, pp. 297-302.

Kranz et al., "In vitro fertilization with isolated, single gametes results in zygotic embryogenesis and fertile maize plants", The Plant Cell, vol. 5, Jul. 1993, pp. 739-746.

Kranz, "In vitro fertilization with isolated single gametes", Methods in Molecular Biology, vol. 111, 1999, pp. 259-267.

Kumlehn et al., "In vitro development of wheat (*Triticum aestivum* L.) from zygote to plant via ovule culture", Plant Cell Reports, vol. 16, 1997, pp. 663-667.

Leduc et al., "Deleterious effect of minimal enzymatic treatments on the development of isolated maize embryo sacs in culture", Sex Plant Reprod, vol. 8, 1995, pp. 313-317.

Leduc et al., "Isolated maize zygotes mimic in vivo embryonic development and express microjected genes when cultured in vitro", Developmental Biology, vol. 177, 1996, pp. 190-203.

Mol et al., "In-vitro culture of fertilized embryo sacs of maize: zygotes and two-celled proembryos can develop into plants", Planta, vol. 189, 1993, pp. 213-217.

Murashige et al., "A revised medium for rapid growth and bio assays with tobacco tissue cultures", Physiol. Plant., 15, 1962, pp. 473-497.

Nelson, "A photometric adaptation of the somogyi method for the determination of glucose", J. Biol. Chem., 153, Feb. 3, 1994, pp. 375-380.

Okamoto, "In vitro fertilization with rice gametes: production of zygotes and zygote and embryo culture", Methods in Molecular Biology, vol. 710, 2011, pp. 17-27.

Shen et al., "Isolation, culture, and transient transformation of plant protoplasts", Current Protocols in Cell Biology, Supplement 63, 2014, pp. 2.8.1-2.8.17.

Somogyi, "Notes on sugar determination", J. Biol. Chem., vol. 195, 1952, pp. 19-23.

Uchiumi et al., "Establishment of an in vitro fertilization system in rice", Planta, vol. 226, 2007, pp. 581-589.

Uchiumi et al., "isolation of gametes and central cells from *Oryza sativa* L.", Sex. Plant Reproduction, vol. 19, 2006, pp. 37-45.

Written Opinion of the international Searching Authority and international Search Report dated Jun. 27, 2017, for international Application No. PCT/JP2017/013868.

Yoo et al., "*Arabidopsis mesophyll* protoplasts: a versatile cell system for transient gene expression analysis", Nature Protocols, vol. 2, No. 7, 2007, pp. 1565-1572.

Zhang et al., "Regeneration of fertile plants from isolated zyaotes of rice (*Oryza sativa*)", Plant Cell Reports, vol. 19, 1999, pp. 128-132.

Zhou et al., "Overexpression of the wheat aquaporin gene, TaAQP7, enhances drought tolerance in transgenic tobacco", PLoS One, vol. 7, No. 12, Dec. 2012, pp. 1-14.

Office Action issued in Russian Application No. 2018138200 dated Jul. 6, 2020 (with Search Report).

Chinese Office Action for corresponding Chinese Application No. 201780018863.3, dated Jan. 19, 2022, with English translation.

Han et al., "Isolation of Egg Cells and Zygote in Oryza Sativa". Acta Botanica Sinica, vol. 40. No. 2, p. 186-188, 1998.

Rhodes et al."Plant Regeneration from Protoplasts Isolated from Embryogenic Maize Cell Cultures", Biotechnology, vol. 6, No. 1, p. 56-60, 1988.

Yanhong Yang, "Isolation of sperm, egg cells, central cells, synergids and proembryonic cells from Torenia foumieri (Lind.)", China Master's Theses Full-text Database (E-journal) Basic Science Series, 2008, issue 8, A006-43.

\* cited by examiner

METHOD FOR INTRODUCING SUBSTANCE INTO PLANT

CROSS-REFERENCE TO RELATED APPLICATIONS

This application is the National Phase of PCT International Application No. PCT/JP2017/013868, filed on Mar. 28, 2017, which claims priority under 35 U.S.C. § 119(a) to Patent Application No. 2016-070288, filed in Japan on Mar. 31, 2016, all of which are hereby expressly incorporated by reference into the present application.

TECHNICAL FIELD

The present invention relates to a method for introducing a substance into a plant.

BACKGROUND ART

Transgenic technologies in plants, particularly, in monocotyledonous plants, have been widely adopted rapidly, since methods using Agrobacterium for rice and maize have been developed in the 1990's, and various transformation methods have been developed so far. However, it is known that the efficiency of transformation greatly differs among species and varieties, since many of such methods need to go through dedifferentiation and regeneration of plant tissues. For certain species and varieties, the efficiency of transformation is low, and transformed plants with reproducibility cannot be obtained. For example, in B73, which is a very important strain for breeding maize, reproducible transformation methods have not been developed yet.

Further, it is becoming possible to efficiently practice a genome editing in recent year. However, practical use of genome editing in plants is also hindered since the point that the ease of tissue culture differs depending on crop species and varieties greatly affects the efficiency of genome editing.

Meanwhile, artificial fertilization in which a sperm cell and an egg cell isolated from plants are artificially fused has been attempted in the 1990's, and plants have been successfully produced. Non-Patent Literature (NPL) 1 discloses a method of producing a fertilized egg cell by electrofusion of an egg cell and a sperm cell of maize and culturing them into plants. In NPL 1, an enzyme mixture (0.75% of pectinase (Serva), 0.25% of pectolyase, 0.5% of hemicellulose, and 0.5% of cellulase) is used for separating an egg cell, where the enzymes used, particularly, pectinase have a high titer. Further, there is no mention that gene introduction and transformation have been performed using a fertilized egg cell produced by using the egg cell.

Further, NPL 2 discloses a method of isolating male and female gametes (an egg cell and a center cell) of rice. Specifically, an enzymatic treatment in a 0.3-M mannitol solution (for 10 to 15 minutes using a mannitol solution (650 mosmol/kg.$H_2O$)+0.3% of pectolyase Y-23, 1.5% of pectinase, 1% of cellulose, and 1% of hemicellulose) is performed after the ovule is isolated from a plant, where the enzymes, particularly, pectinase have a high titer, in the same manner as in NPL 1. Further, the target is not a fertilized egg but an egg cell before fertilization, and there is no mention that regeneration to a plant, and gene introduction and transformation into a plant have been performed.

NPL 3 and NPL 4 disclose methods of producing fertilized eggs by electrofusion of male and female gametes of rice and culturing them into plants. These prior art literatures indicate that plants can be induced from a fertilized egg cell obtained by artificially fusing male and female gametes. However, also in the aforementioned literatures, gene introduction and transformation are not mentioned at all, in the same manner as in NPL 2, and it has been unknown whether or not transformation can be performed using fertilized eggs. In NPLs 3 and 4, there is also no mention about performing the enzymatic treatment of an egg cell.

In species such as maize (NPLs 5 and 12), rice (NPLs 6 and 11), wheat (NPL 7), barley (NPLs 8 and 10), and tobacco (NPL 9), examples in which fertilized eggs are collected and cultured from the embryo sac after fertilization to produce plants are known. In some of the examples, it has been reported that DNA can be introduced into a fertilized egg cell by the microinjection method, as in NPLs 5 and 10, but it has not been reported that the method has been put to practical use. Further, gene introduction by other methods has not been found at all.

Examples of the method for introducing genes into a plant cell include the polyethylene glycol method (polyethylene glycol: PEG method) and the electroporation method, other than the microinjection method. Among them, the microinjection method enables gene introduction into a cell having a cell wall and does not particularly need to remove the cell wall of a plant cell by an enzymatic treatment or the like. However, there is a disadvantage that only one cell can be handled in a one-time introduction. In contrast, the electroporation method and the PEG method, particularly, the PEG method have an advantage that a lot of cells can be handled at one time, as compared with the microinjection method, but need a process of removing cell walls using an enzyme or the like. For a fertilized egg cell, a method for removing a cell wall with cell activity being maintained, so as to enable continuous cell division after the removal of the cell wall and growth to a plant has been unknown. Therefore, it has not been reported that gene introduction to a fertilized egg cell is performed by a method such as the PEG method to achieve cell division. Among the aforementioned reports, the fertilized egg cells of rice, wheat, and barley are released using only glass needles or the like, without using enzymes to remove a cell wall such as cellulases. Since a cell wall remains in such fertilized eggs isolated by a physical approach, application of the PEG method is inferred to be difficult, and no examples of application of the PEG method have been reported in fact.

In the removal of a cell wall by the enzymatic treatment, it is conventionally known that treatments with cell wall-degrading enzymes, such as celluloses and pectinase, are effective for protoplastization of a plant cell. However, a high-concentration or long-term treatment may possibly cause an adverse effect on a plant cell. Meanwhile, a low-concentration or short-term treatment may fail to achieve the desired purpose of protoplastization, due to the cell wall being incompletely removed. Therefore, even in maize for which isolation and culture of an egg cell and a fertilized egg cell have been studied comparatively much in plants, there are no examples of gene introduction by the PEG method through protoplastization of a fertilized egg cell, and whether or not such gene introduction is possible has been unknown.

Actually, NPL 5 discloses that gene introduction has been performed by microinjection, in which fertilized eggs are isolated by enzymatic treatment of maize for a very short time (for 2 minutes). Further, NPL 9 discloses a two-step enzymatic treatment for a total of one hour at maximum, using tobacco as a material and Macerozyme R10 having a very weak pectinase activity. It is inferred that the reason why such an exceptionally short-term enzymatic treatment or long-term enzymatic treatment with a very weak enzyme is performed, as in the two methods disclosed in NPLs 5 and 9, is to minimize the negative effects on a fertilized egg cell since the enzymatic treatments are considered to cause negative effects on the activity and development capacity. However, it is considered that a cell wall of a fertilized egg cell is not completely removed by short-term enzymatic treatments or enzymatic treatments with weak activity, and thus the fertilized egg cell is unsuitable as materials in the PEG method. Therefore, there have been no examples of application of the PEG method to fertilized eggs, and whether or not a fertilized egg cell subjected to the PEG method can maintain the division capacity has been unknown.

CITATION LIST

Non Patent Literature

NPL 1: Kranz, E. and Lorz, H., (1993), Plant Cell 5: 739-746
NPL 2: Uchiumi, T. et al., (2006), Sex. Plant Reprod. 19: 37-45
NPL 3: Uchiumi, T. et al., (2007), Planta 226: 581-589
NPL 4: Okamoto, T., (2011), Methods Mol. Biol. 710: 17-27
NPL 5: Leduc, N. et al., (1996), Developmental Biology 177: 190-203
NPL 6: Zhang, J. et al., (1999), Plant Cell Reports 19: 128-132
NPL 7: Kumhehn, J. et al., (1997), Plant Cell Reports 16: 663-667
NPL 8: Holm, P. B. et al., (1994), The Plant Cell 6: 531-543
NPL 9: Yuchi, H. E. et al., (2004), Chinese Science Bulletin 49: 810-814
NPL 10: Holm, P. B. et al., (2000), Transgenic Research 9: 21-32
NPL 11: Abiko, et al., (2013), Journal of Experimental Botany 64: 1927-1940
NPL 12: Leduc, et al., (1995), Sex Plant Reprod. 8: 313-317
NPL 13: Yoo, et al., (2007), Nat Protoc. 2 (7): 1565-72
NPL 14: Ishii, S., (1976), Phytopatholory, 66, 281-289
NPL 15: Nelson, N., (1944), J. Biol. Chem., 153, 375-380
NPL 16: Somogyi, M., (1952), J. Biol. Chem. 195, 19-23
NPL 17: Murashike, T., and Skoog, F., (1962) Physiol. Plant. 15: 473-497
NPL 18: Gamborg, O. L. et al., (1968) Exp. Cell Res. 50: 151-158
NPL 19: Chu, et al., (1975) Sci. Sinica 18: 659-668
NPL 20: Mol, R. et al., (1993) Planta 189: 213-217
NPL 21: Kranz, et al., (1991) Sex. Plant Reprod. 4: 12-16
NPL 22: Kranz, E., (1999), Methods Mol. Biol. 111: 259-67.

SUMMARY OF INVENTION

Technical Problem

It is an object of the present invention to provide a method for introducing a substance into a plant, and a plant into which a substance is introduced by the method of the present invention.

A fertilized egg is a cell that originally possesses the ability to grow into a plant and therefore is expected not to be affected by the culture efficiency due to the difference between species or varieties. Transformation and genome editing can be performed on a wider variety of species or crops by introducing substances into such a fertilized egg cell as a target than in the current situation. As a result of diligent studies, the inventors have found a method for protoplastization without losing the activity of the fertilized egg cell and further have found that introduction of substances into the fertilized egg cell, induction of division, and transformation are possible by combining a method for efficiently isolating a fertilized egg and a method for culturing the isolated a fertilized egg cell, thereby achieving the present invention.

Solution to Problem

The present invention includes, though not limited to, the following embodiments.

EMBODIMENT 1

A method for introducing a substance into a plant, comprising the steps of:
obtaining an enzymatically treated and isolated fertilized egg cell by
(1-i) isolating a fertilized egg cell from a plant tissue containing a fertilized egg cell, and then treating the fertilized egg cell with an enzyme solution containing a plant tissue-degrading enzyme under a low-titer condition,
(1-ii) treating a plant tissue containing a fertilized egg cell with an enzyme solution containing a plant tissue-degrading enzyme under a low-titer condition, and then isolating the fertilized egg cell that has been enzymatically treated, or
(1-iii) treating a plant tissue containing a fertilized egg cell with an enzyme solution containing a plant tissue-degrading enzyme under a low-titer condition, and simultaneously isolating the fertilized egg cell that has been enzymatically treated; and
(2) introducing a substance selected from the group consisting of nucleic acids, proteins, and peptides into the resultant enzymatically treated and isolated fertilized egg cell.

EMBODIMENT 2

A method for introducing a substance into a plant, comprising the steps of:
obtaining an enzymatically treated and isolated fertilized egg cell by
(1-iv) isolating an egg cell and a sperm cell from a plant, fusing the cells to produce a fertilized egg, and then treating the fertilized egg cell with an enzyme solution containing a plant tissue-degrading enzyme under a low-titer condition, or
(1-v) treating a plant tissue containing an egg cell with an enzyme solution containing a plant tissue-degrading enzyme under a low-titer condition, and then isolating the egg cell that has been enzymatically treated, and further fusing the egg cell with an isolated sperm cell; and
(2) introducing a substance selected from the group consisting of nucleic acids, proteins, and peptides into the resultant enzymatically treated and isolated fertilized egg cell.

EMBODIMENT 3

The method according to embodiment 1 or 2, wherein the plant tissue-degrading enzyme is selected from the group consisting of pectinases, cellulases, proteases, hemicellulases, glucuronidases, zymolyases, chitinases, glucanases, xylanases, galactanases, arabinanases, and lignin-degrading enzymes, and mixtures of these mixtures of two or more of these enzyme groups.

EMBODIMENT 4

The method according to any one of embodiments 1 to 3, wherein the plant tissue-degrading enzyme comprises a pectinase.

EMBODIMENT 5

The method according to any one of embodiments 1 to 4, wherein the plant is a monocotyledonous plant.

EMBODIMENT 6

The method according to embodiment 5, wherein the plant is selected from the group consisting of maize, wheat, barley, rice, and sorghum.

EMBODIMENT 7

The method according to any one of embodiments 1 to 6, wherein the plant is maize B73 or a maize variety derived from B73.

EMBODIMENT 8

The method according to any one of embodiments 1 to 6, comprising isolating an egg cell from a plant tissue containing an egg cell and then fusing the egg cell with a sperm cell to produce a fertilized egg cell.

EMBODIMENT 9

The method according to any one of embodiments 1 to 8, wherein the enzymatic treatment time is 3 minutes or more and 60 minutes or less.

EMBODIMENT 10

The method according to embodiment 9, wherein the substance introduction of step (2) is performed within 120 minutes after the enzymatic treatment.

EMBODIMENT 11

The method according to embodiment 8 or 9, wherein the substance introduction of step (2) is performed within 120 minutes after the fusion with a sperm cell.

EMBODIMENT 12

The method according to embodiment 9, wherein the plant tissue-degrading enzyme comprises a pectinase, and the unit(s)/mL of the pectinase in the system during the enzymatic treatment of step (1) is 60 or less.

EMBODIMENT 13

The method according to any one of embodiments 1 to 12, wherein the plant tissue-degrading enzyme comprises a pectinase, and the unit(s)/mL of the pectinase in the system during the enzymatic treatment of step (1) multiplied by the treatment time is 310 or less.

EMBODIMENT 14

The method according to any one of embodiments 1 to 13, wherein the substance introduction of step (2) is performed using a PEG method or an electroporation method.

EMBODIMENT 15

A method for introducing a substance into a plant, comprising the steps of:
obtaining an enzymatically treated and isolated fertilized egg cell by
(1-i) isolating a fertilized egg cell from a plant tissue containing a fertilized egg cell, and then treating the fertilized egg cell with an enzyme solution containing a plant tissue-degrading enzyme under a low-titer condition,
(1-ii) treating a plant tissue containing a fertilized egg cell with an enzyme solution containing a plant tissue-degrading enzyme under a low-titer condition, and then isolating the fertilized egg cell that has been enzymatically treated, or
(1-iii) treating a plant tissue containing a fertilized egg cell with an enzyme solution containing a plant tissue-degrading enzyme under a low-titer condition, and simultaneously isolating the fertilized egg cell that has been enzymatically treated;
(2) introducing a substance selected from the group consisting of nucleic acids, proteins, and peptides into the resultant enzymatically treated and isolated fertilized egg cell;
(3) conducting callus formation or embryo-like structure formation of the fertilized egg cell into which the substance has been introduced; and
(4) regenerating the callused or embryonated tissue in a regeneration medium.

EMBODIMENT 16

A method for introducing a substance into a plant, comprising the steps of:
obtaining an enzymatically treated and isolated fertilized egg cell by
(1-iv) isolating an egg cell and a sperm cell from a plant, fusing the cells to produce a fertilized egg, and then treating the fertilized egg cell with an enzyme solution containing a plant tissue-degrading enzyme under a low-titer condition, or
(1-v) treating a plant tissue containing an egg cell with an enzyme solution containing a plant tissue-degrading enzyme under a low-titer condition, and then isolating the egg cell that has been enzymatically treated, and further fusing the egg cell with an isolated sperm cell;
(2) introducing a substance selected from the group consisting of nucleic acids, proteins, and peptides into the resultant enzymatically treated and isolated fertilized egg cell;
(3) conducting callus formation or embryo-like structure formation of the fertilized egg cell into which the substance has been introduced; and
(4) regenerating the callused or embryonated tissue in a regeneration medium.

EMBODIMENT 17

A substance-introduced plant obtained by the method according to any one of embodiments 1 to 16.

Advantageous Effects of Invention

The present invention has enabled culture, substance introduction, and transformation of plants, which have been conventionally difficult to culture, such as maize B73. This enables transformants of plants, which have been difficult to transform and thus to which useful traits could not be given, to be stably obtained with good reproducibility.

BRIEF DESCRIPTION OF DRAWINGS

The patent or application file contains at least one color drawing. Copies of this patent or patent application publication with color drawing will be provided by the USPTO upon request and payment of the necessary fee.

DESCRIPTION OF EMBODIMENTS

Figure 1:
FIG. 1 is a transmission image of a dissected nucellus tip of maize (B73) after an enzymatic treatment.
Figure 2:
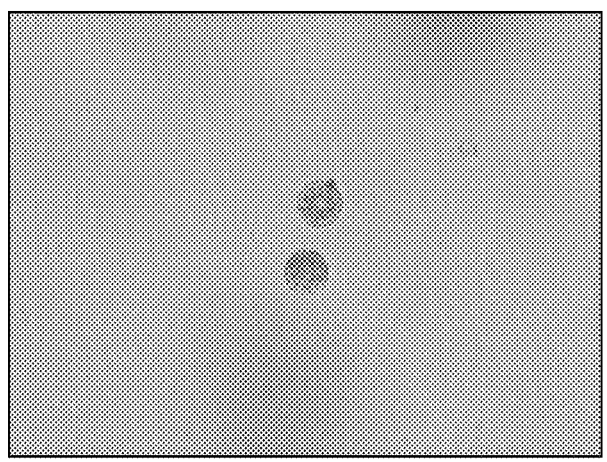
FIG. 2 is an optical micrograph of isolated fertilized egg cells of maize (B73).
Figure 3:
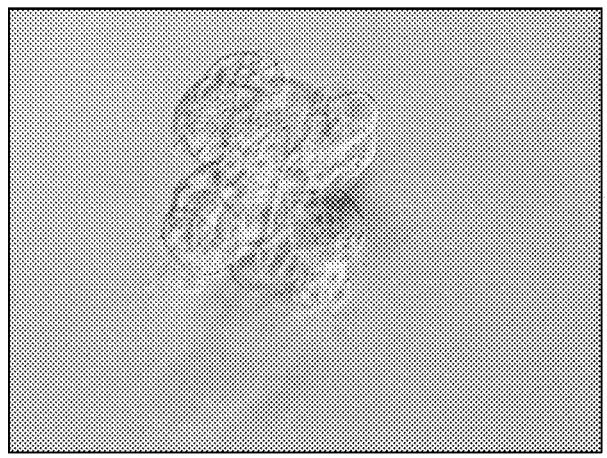
FIG. 3 is an optical micrograph of an embryonic cell mass derived from a fertilized egg cell of maize (B73) that has started to divide.
Figure 4:
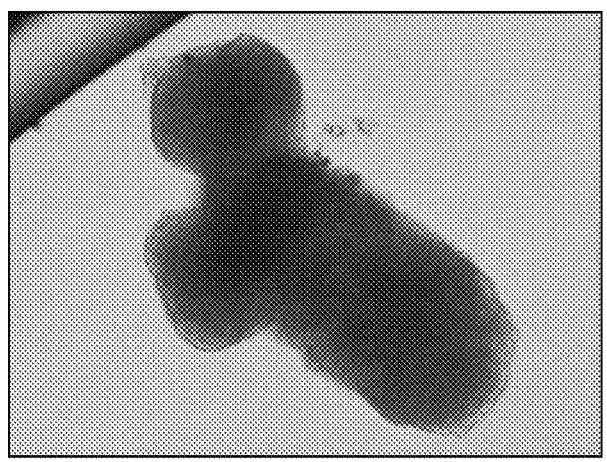
FIG. 4 is an optical micrograph of an embryonic cell mass derived from the fertilized egg cell of maize (B73) of FIG. 3 that has grown.
Figure 5:
FIG. 5 is an optical micrograph of a shoot generated from the embryonic cell mass of the maize (B73) of FIGS. 3 and 4.

The present invention relates to a method for introducing a substance into a plant.

The method of the present invention comprises the steps of:

obtaining an enzymatically treated and isolated fertilized egg cell by (1-i) isolating a fertilized egg cell from a plant tissue containing a fertilized egg cell, and then treating the fertilized egg cell with an enzyme solution containing a plant tissue-degrading enzyme under a low-titer condition, (1-ii) treating a plant tissue containing a fertilized egg cell with an enzyme solution containing a plant tissue-degrading enzyme under a low-titer condition, and then isolating the fertilized egg cell that has been enzymatically treated, or (1-iii) treating a plant tissue containing a fertilized egg cell with an enzyme solution containing a plant tissue-degrading enzyme under a low-titer condition, and simultaneously isolating the fertilized egg cell that has been enzymatically treated; and (2) introducing a substance selected from the group consisting of nucleic acids, proteins, and peptides into the resultant enzymatically treated and isolated fertilized egg cell.

According to another embodiment, the method of the present invention comprises the steps of:

obtaining an enzymatically treated and isolated fertilized egg cell by (1-iv) isolating an egg cell and a sperm cell from a plant, fusing the cells to produce a fertilized egg, and then treating the fertilized egg cell with an enzyme solution containing a plant tissue-degrading enzyme under a low-titer condition, or (1-v) treating a plant tissue containing an egg cell with an enzyme solution containing a plant tissue-degrading enzyme under a low-titer condition, and then isolating the egg cell that has been enzymatically treated, and further fusing the egg cell with an isolated sperm cell; and (2) introducing a substance selected from the group consisting of nucleic acids, proteins, and peptides into the resultant enzymatically treated and isolated fertilized egg cell.

According to still another embodiment, the method of the present invention comprises the steps of:

obtaining an enzymatically treated and isolated fertilized egg cell by (1-i) isolating a fertilized egg cell from a plant tissue containing a fertilized egg cell, and then treating the fertilized egg cell with an enzyme solution containing a plant tissue-degrading enzyme under a low-titer condition, (1-ii) treating a plant tissue containing a fertilized egg cell with an enzyme solution containing a plant tissue-degrading enzyme under a low-titer condition, and then isolating the fertilized egg cell that has been enzymatically treated, or (1-iii) treating a plant tissue containing a fertilized egg cell with an enzyme solution containing a plant tissue-degrading enzyme under a low-titer condition, and simultaneously isolating the fertilized egg cell that has been enzymatically treated;

(2) introducing a substance selected from the group consisting of nucleic acids, proteins, and peptides into the resultant enzymatically treated and isolated fertilized egg cell;

(3) conducting callus formation or embryo-like structure formation of the fertilized egg cell into which the substance has been introduced; and (4) regenerating the callused or embryonated tissue in a regeneration medium.

According to still another embodiment, the method of the present invention comprises the steps of:

obtaining an enzymatically treated and isolated fertilized egg cell by (1-iv) isolating an egg cell and a sperm cell from a plant, fusing the cells to produce a fertilized egg, and then treating the fertilized egg cell with an enzyme solution containing a plant tissue-degrading enzyme under a low-titer condition, or (1-v) treating a plant tissue containing an egg cell with an enzyme solution containing a plant tissue-degrading enzyme under a low-titer condition, and then isolating the egg cell that has been enzymatically treated, and further fusing the egg cell with an isolated sperm cell;

(2) introducing a substance selected from the group consisting of nucleic acids, proteins, and peptides into the resultant enzymatically treated and isolated fertilized egg cell;

(3) conducting callus formation or embryo-like structure formation of the fertilized egg cell into which the substance has been introduced; and (4) regenerating the callused or embryonated tissue in a regeneration medium.

Plant

The types of a plant are not specifically limited. Any one of dicotyledonous plants and monocotyledonous plants may be employed, preferably, monocotyledonous plants are employed. Further preferably, maize, wheat, barley, rice, sorghum, rye, and the like are employed, most preferably, maize, wheat, and rice are employed.

The method of the present invention can be particularly used for, though not limited to, "difficult-to-culture" plants or varieties. The term "difficult-to-culture", for example, means that culture is difficult, specifically, culture of cells isolated from a plant is difficult, or callus formation by a treatment such as dedifferentiation, or regeneration from a callus to a plant is difficult.

Generally, culture of monocotyledonous plants is more difficult than that of dicotyledonous plants, but the "difficult-to-culture" plants, for example, include soybeans, common beans, capsicums, and the like. The difficult-to-culture varieties mean varieties culture of which is more difficult than that of general research varieties (such as maize A188) of the same species. Examples thereof include maize B73, maize elite varieties derived from B73, wheat elite varieties (such as AC Barrie and TAM), barley varieties other than GoldenPromise and Igri, and sorghum varieties other than 296B, C401, SA281, P898012, Pioneer 8505, and Tx430.

Fertilized Egg Cell

In the present invention, the cell into which the substance is introduced is preferably a zygote, i.e., a fertilized egg cell. The fertilized egg cell may be a fertilized egg cell that is isolated from a tissue of a plant containing the embryo sac (such as ovary, ovule, and nucellus), i.e., a fertilized egg cell isolated from a plant that has been pollinated and fertilized. Alternatively, a fertilized egg cell may be produced and obtained by a fusing egg cell and a sperm cell isolated from a plant before pollinated and fertilized. That is, the enzymatically treated and isolated fertilized egg cell can be obtained by any of (1-i) isolating a fertilized egg cell from a plant tissue containing a fertilized egg cell, and then treating the fertilized egg cell with an enzyme solution containing a plant tissue-degrading enzyme under a low-titer condition, (1-ii) treating a plant tissue containing a fertilized egg cell with an enzyme solution containing a plant tissue-degrading enzyme under a low-titer condition, and then isolating the fertilized egg cell that has been enzymatically treated, or (1-iii) treating a plant tissue containing a fertilized egg cell with an enzyme solution containing a plant tissue-degrading enzyme under a low-titer condition, and simultaneously isolating the fertilized egg cell that has been enzymatically treated;

(1-iv) isolating an egg cell and a sperm cell from a plant, fusing the cells to produce a fertilized egg, and then treating the fertilized egg cell with an enzyme solution containing a plant tissue-degrading enzyme under a low-titer condition, or (1-v) treating a plant tissue containing an egg cell with an enzyme solution containing a plant tissue-degrading enzyme under a low-titer condition, and then isolating the egg cell that has been enzymatically treated, and further fusing the egg cell with an isolated sperm cell.

The (fertilized) egg cell can be isolated using a glass capillary or the like by cutting a tissue containing the embryo sac (such as ovule) in a solution with a suitable osmotic pressure and putting the cell exposed on the cut surface under a microscope. In this case, enzymatically treated fertilized egg is obtained by treating the isolated (fertilized) egg cell with an enzyme solution for a certain time.

Alternatively, the egg cell can be mechanically released to be isolated, for example, by dissecting a tissue such as nucellus using glass needles or the like under a microscope, after the tissue containing the embryo sac such as ovule is treated with an enzyme solution for a certain time. In this case, enzymatically treated (fertilized) egg can be obtained without the subsequent enzymatic treatment. In the case where fertilized egg is obtained by fusing the isolated egg cell and a sperm cell, the enzymatic treatment may be performed either before or simultaneously with the isolation of the egg cell, or after the fusion with the sperm cell.

Enzymatic Treatment

The method of the present invention features treating (fertilized) egg cell or a tissue of a plant containing (fertilized) egg cell with an enzyme solution containing a plant tissue-degrading enzyme under a low-titer condition. The enzymatic treatment may be performed at any timing before the isolation of the (fertilized) egg cell from the tissue, simultaneously with the isolation, or after the isolation, but is preferably performed simultaneously with the isolation or after the isolation.

(i) Types of Enzyme

In a cell wall of plants, a basic skeleton consisting of celluloses is embedded in a substrate (matrix or substrate gel) consisting of other polysaccharides or proteins. Polysaccharides constituting the substrate are classified into pectins traditionally extracted using hot water or acidic buffers and hemicelluloses that are alkali-soluble components but are often collectively referred to as matrix polysaccharides recently.

The cell walls of most of angiosperm plants are called type I, where cellulose and xyloglucan are mostly included, and pectin, arabinoxylan, glucomannan, galactoglucomannan, and the like are included. Meanwhile, cell walls of some of monocotyledonous (Poales) are called type II, where cellulose, xylan (glucuronoarabinoxylan), and 1,3-1,4-β-D-glucan are mostly included, and pectin and xyloglucan are less. In the cell walls of type I, structural proteins (such as extensin) play a big role, whereas in the cell walls of type II, the content of proteins is low, and crosslinking of phenol acids (such as ferulic acid) serves as an alternative.

Enzymes used in the method of the present invention are not specifically limited as long as they are plant tissue-degrading enzymes. The "plant tissue-degrading enzymes" generally refer to enzymes that directly or indirectly affect pectins, celluloses, hemicelluloses, and other matrix polysaccharides, phospholipids, proteins, and the like, in the periphery of plant tissues and cells to degrade them. Examples thereof include, though not limited to, enzymes for protoplast preparation, phospholipases that degrade cell membranes, tannases considered to be useful for tissue degradation, ferulic acid esterases that degrade components contained in cell walls of type II such as rice, and proteases. In particular, various enzymes for protoplast preparation used for dissolving a cell wall of a plant cell to prepare a protoplast can be used.

Examples thereof include pectinases, cellulases, proteases, hemicellulases (where hemicellulases generally refer to enzymes that hydrolyze hemicelluloses), glucuronidases, zymolyases, chitinases, glucanases, xylanases, galactanases, arabinanases and lignin-degrading enzymes, or mixtures of these (mixtures of two or more of these enzyme groups). Pectinases, for example, include polygalacturonase (galacturonase), pectin lyase, and pectin methyl esterase. In this description, the titer of pectinases means the sum of the potencies of these three kind of enzymes or the potencies of the two enzymes, polygalacturonase and pectin lyase, unless otherwise specified.

Preferably, the plant tissue-degrading enzyme contains a pectinase. Only a pectinase may be contained, or a pectinase and one or more types of enzymes selected from the aforementioned group may be contained. Preferably, cellulases and pectinases are contained.

Pectins are a kind of complex polysaccharides mainly containing polygalacturonic acid in which galacturonic acids are bonded through α-1,4 linkages. Pectinases that are the degrading enzymes thereof generally refer to a group of enzymes that catalyze the enzyme reaction system that degrades pectins and are classified into (a) polygalacturonase that hydrolyzes the α-1,4 linkages of pectins or polygalacturonic acid, (b) pectin lyase (polygalacturonic acid lyase) that degrades the main chain by elimination reaction, and (c) pectin methyl esterase that hydrolyzes methyl esters of pectins. Pectinases are enzymes that affect the bounding region (middle layers) between individual cells in plant tissues to break down the tissues into single cells and are important, particularly, in plant cell engineering and maceration in which plant cells are released without breakdown. Examples of the pectinases include those containing polygalacturonase such as product name Macerozyme R10 (trademark) (manufactured by Yakult Honsha Co., Ltd.) and Sumiteam AP2 (manufactured by SHINNIHON CHEMICALS Corporation), and those containing pectin lyase such as Pectolyase Y23 (manufactured by Morishin Pharmaceutical Co., Ltd.) and Pectinase (manufactured by Sigma-Aldrich). Preferably, a mixture of Macerozyme R10 and Pectolyase Y23, or pectinase Y23 alone is used.

Cellulases are enzymes that hydrolyze glycosidic bonds of β-1,4-glucan of celluloses as components of plant cell walls. Examples of cellulases to be used include product name Cellulase OnozukaRS (trademark) (manufactured by Yakult Honsha Co., Ltd.), Cellulase OnozukaR10 (manufactured by Yakult Honsha Co., Ltd.), and Driselase (manufactured by KYOWA HAKKO BIO CO. LTD). Preferably, Cellulase OnozukaRS (trademark) and Cellulase (Worthington), further preferably, Cellulase (Worthington) are used.

(ii) Titer (Units) of Enzymes

In the method of the present invention, the plant tissue-degrading enzymes with which a fertilized egg cell of plants is treated are used under "low-titer condition".

The "low-titer condition" means a condition in which the enzymes function less than in conditions generally in enzyme use for degrading plant tissues (in the present invention using degrading enzymes, the condition in which the enzyme activity to degrade the target substance is low), specifically; a short treatment time and/or a low enzyme concentration (low enzyme activity: low units/mL). In particular, a shorter treatment time and/or a lower concentration than in common conditions for protoplast preparation are preferable. The condition corresponding to the "low-titer condition" can be appropriately changed depending on the types of enzymes and the types of plants to be used.

Known methods can be used for measuring the units. For example, the pectin lyase activity can be measured according to the method of Ishii, et al (NPL 14), and one unit of pectin lyase activity can be an amount in which unsaturated polygalacturonide corresponding to 1 μmol of unsaturated digalacturonide is produced in one minute. Further, the polygalacturonase activity can be measured according to the Somogyi-Nelson method (NPL 15 and NPL 16), and one unit of galacturonase activity can be an amount in which 1 μmol of galacturonic acid (or the derivatives and modified products thereof) is produced in one minute.

In EXAMPLES of the present description, it has been found that pectinases, which have been considered to affect binding between cells in plant tissues, exert a great influence not only on the isolation of a fertilized egg that is a single cell but also on an ability to subsequently regenerate to a plant. It has been found that, when the concentration of pectinases contained in the enzyme solution used for the enzymatic treatment of a fertilized egg cell is low, the isolated fertilized egg cell can be regenerated to plants or/and substances such as nucleic acids can be introduced thereinto. In particular, in maize B73, culture of which has been difficult, especially, callus formation and plant regeneration of which have been difficult by conventional methods, it could be confiitned that, when the unit(s)/mL of pectinases contained in the enzyme solution is 60 or less, and the unit(s)/mL multiplied by the time is 310 or less, an embryonic cell mass can be obtained. Further, it could be confirmed that nucleic acids can be introduced by the PEG method, and regeneration to plants can be achieved.

Accordingly, in the present invention, in the case where the plant tissue-degrading enzyme is a pectinase, the unit(s)/mL of the pectinase in the system during the enzymatic treatment of step (1), that is, the low-titer treatment condition in the present invention is preferably, though not limited to, 60 or less, 40 or less, 20 or less, 15 or less, 10 or less, 9 or less, 8 or less, 7 or less, 6 or less, 5 or less, 4 or less, 3 or less, 2 or less, 1 or less, 0.7 or less. In the case where the unit(s)/mL of pectinase in the enzyme solution is 60 or more, the (fertilized) egg cell is damaged, which is therefore unpreferable. The lower limit of the unit(s)/mL is not specifically limited. Preferably, it is 0.1 or more, 0.2 or more, 0.4 or more, 0.5 or more, 0.6 or more, or 0.65 or more. The unit(s)/mL multiplied by the time is preferably 310 or less, 300 or less, 250 or less, 200 or less, 100 or less, 90 or less, 50 or less, or 30 or less. The lower limit of the unit(s)/mL multiplied by the time is not specifically limited. Preferably, it is 1 or more, 2 or more, 3 or more, 3.3 or more, 5 or more, 10 or more, 15 or more, or 20 or more.

(iii) Enzymatic Treatment Time

The enzymatic treatment time is preferably, though not limited to, 3 minutes or more, more preferably 5 minutes or more. Preferably, it is 60 minutes or less, 50 minutes or less, or 45 minutes or less. More preferably, it is 3 minutes or more and 60 minutes or less, 5 minutes or more and 50 minutes or less, or 5 minutes or more and 45 minutes or less.

In a short-term treatment with a dense (high-units/mL or high-titer) enzyme solution, a difference occurs in the results of the enzymatic treatment depending on the individual, which is not preferable. Specifically, this is because a part of the ovary or ovule containing the embryo sac of a plant is first cut out with a razor or the like for isolating a (fertilized) egg cell, for example, where the distance from the cut end (in the case of a mechanical process, a (fertilized) egg cell can be pushed out through the cut end, for example, by a process such as pressing the ovule) to the (fertilized) egg cell varies depending on the ovule. In particular, in the case where the distance from the cut end to the (fertilized) egg cell is long, it takes time for the enzyme solution to permeate therethrough to be in contact with the (fertilized) egg cell. Such a time loss shortens the actual time to enzymatically treat the (fertilized) egg cell, in the case of a short-term treatment with a dense enzyme solution, and therefore the efficacy of the enzymatic treatment differs for each ovule, resulting in so-called unevenness. The substance introduction efficiency into (fertilized) eggs derived from ovules that are almost not enzymatically treated (as compared with cases of a low enzyme concentration multiplied by a long-term treatment) decreases, as a result of which the transformation efficiency decreases.

In contrast, in the case of a long-term treatment with a dilute enzyme solution, even if the distance from the cut end to the (fertilized) eggs differs to some extent, the enzyme solution has enough time to sufficiently permeate into the (fertilized) eggs, and therefore the enzymatic treatment is sufficiently performed. Therefore, the unevenness in the degree of the enzymatic treatment for each ovule decreases, and the substance introduction efficiency is improved, resulting in an improvement in transformation efficiency. Thus, it is important to perform the treatment for a certain time or more. Meanwhile, the long-term treatment is also not preferable since it reduces the cell activity of fertilized eggs.

Protoplast preparation generally requires a long time (4 hours or more). The enzymatic treatment of the present invention is performed obviously in a shorter time than the enzymatic treatment time for protoplast preparation.

(iv) Other Conditions for Enzymatic Treatment

In the enzymatic treatment, the osmotic pressure is preferably adjusted. The method for adjusting the osmotic pressure is not specifically limited, but the osmotic pressure is adjusted by adding an osmolyte, for example. Specifically, the osmotic pressure is adjusted by adding polyhydric alcohols, amino acids, or the like. Addition of polyhydric alcohols is preferable, and mannitol, maltose, glucose, sorbitol, raffinose, trehalose, and oligosaccharide can be preferably, but not restrictively, used.

The preferable osmotic pressure can be appropriately selected depending on the variety of plants to be used. For example, in the case of rice, the lower limit is preferably 380 mosmol/kg $H_2O$ or more, more preferably 390 mosmol/kg $H_2O$ or more, further preferably 400 mosmol/kg $H_2O$ or more. Further, the upper limit is preferably 470 mosmol/kg $H_2O$ or less, more preferably 460 mosmol/kg $H_2O$ or less, further preferably 450 mosmol/kg $H_2O$ or less. In the case of maize, the lower limit is preferably 600 mosmol/kg $H_2O$ or more, further preferably 630 mosmol/kg $H_2O$ or more. Further, the upper limit is preferably 700 mosmol/kg $H_2O$ or less, further preferably 680 mosmol/kg $H_2O$ or less.

The pH is not particularly limited as long as it falls within a pH range that allows production of a protoplast. The pH is preferably 5.0 or more and 7.0 or less. The temperature for the enzymatic treatment can be appropriately set depending on the enzymes to be used. However, in the condition of less than 10° C., the enzyme activity as expected cannot be sufficiently obtained in many enzymes, and therefore 10° C. or more is preferable.

Introducing Substance

The method for introducing a substance into a plant of the present invention comprises a step of introducing a substance selected from the group consisting of nucleic acids, proteins, and peptides into the resultant enzymatically treated and isolated fertilized egg cell (step (2)).

In the present invention, the substance introduced into the plant is selected from the group consisting of nucleic acids, proteins, and peptides. The nucleic acids are not specifically limited and may be RNAs, DNAs, and conjugates or mixtures of both. Preferably, the nucleic acids are circular DNA like vectors, linear DNA, circular RNA, or linear RNA. Those having any length corresponding to the transformation method to be used can be used. For example, in the case of using the PEG method, the length of the nucleic acids is preferably 100 kb or less, more preferably 50 kb or less. Further preferably, the length is 30 kb or less, most preferably 20 kb or less.

Proteins such as nucleases, e.g., ZFN (Zinc Finger Nuclease), TALEN (Transcription Activator-Like Effector Nuclease), and Cas9 nuclease, modifying enzymes, and antibodies, and composites thereof also can be introduced for genome editing. The size of proteins is preferably, though not limited to, a molecular weight of 300 kDa or less, more preferably 200 kDa or less. Chemical substances that are necessary for proteins introduced into the plant to function within the cell, like coenzymes, also may be included.

Peptides generally refer to molecules in which various amino acids are linked in a fixed order by amide bonds (also referred to as "peptide bonds") and generally have a shorter length than proteins. Preferably, the length is 100 a.a. or less, more preferably 50 a.a. or less.

Two or more types of nucleic acids, proteins, and peptides may be introduced. Different types of substances such as nucleic acids with proteins may be introduced.

The method for introducing a substance into a plant is not specifically limited, as long as it is a known method by which a desired substance can be introduced into a plant, and can be appropriately selected corresponding to the types of plants. For example, physicochemical methods (direct DNA introduction methods) such as the polyethylene glycol method (PEG method), the electroporation method, the particle gun method, the microinjection method, and the whisker method, or biological methods (indirect DNA introduction methods) such as the Agrobacterium method can be preferably used. The method of the present invention features treating a fertilized egg cell derived from a plant tissue containing the fertilized egg cell with an enzyme solution containing a plant tissue-degrading enzyme under a low-titer condition. Therefore, the method used in the step of introducing the substance is preferably a method using a plant with its cell wall enzymatically degraded (protoplast). Preferably, the method is the PEG method or the electroporation method, most preferably the PEG method.

The PEG method is a method for incorporating DNA into a plant cell by allowing polyethylene glycol (PEG) to affect a protoplast. The mechanism of DNA uptake has not been known yet. The PEG method can be carried out according to a known protocol as disclosed, for example, in NPL 13.

The electroporation method is a method for transforming a cell by applying an electric pulse to a cell suspension to make small holes through cell membranes and sending DNA in the cell suspension into the cell. In the case of using a plant cell as a material, a protoplast with their cell wall broken and removed is generally used. However, transformation using a cell having a cell wall is also possible, which is called the electroinjection method. In the electroporation method and the electroinjection method, co-transformation can be carried out by dissolving two or more types of DNAs in a suspension and applying an electric pulse in the presence of a plant cell.

Before fertilization, an egg cell has a cell wall in a state different from that of a general somatic cell, and a complete cell wall is formed only when the egg cell is fused with a sperm cell. Particularly, in gene introduction by the PEG method, it is generally essential to an enzymatically treat plant cell to form a protoplast, and the cell wall of the protoplast thus obtained may be regenerated over time in some cases, so that the protoplast returns to a plant cell having a complete cell wall. Therefore, also in the case of using enzymes for isolating a fertilized egg cell from the ovule or the like, it is preferable to rapidly perform the substance introduction operation after the isolation.

Accordingly, the time to the substance introduction is preferably 120 minutes or less, 60 minutes or less, 40 minutes or less, 20 minutes or less, from the enzymatic treatment. Alternatively, in the case of performing the fusion with a sperm cell after the enzymatic treatment, the time to the substance introduction is preferably 120 minutes or less, 60 minutes or less, 40 minutes or less, 20 minutes or less, after the cell fusion.

Callus formation or embryo-like structure formation (forming embryonic cell mass) and regeneration The method for introducing a substance into a plant of the present invention may further comprise: (3) conducting callus formation or embryo-like structure formation (forming an embryonic cell mass) of the fertilized egg cell into which the substance has been introduced, after the step of introducing the substance (step (2)); and (4) regenerating the callused or embryonated tissue in a regeneration medium.

The callus formation or embryo-like structure formation step of step (3), and the regeneration step of step (4) are not specifically limited, and known methods for regenerating a plant from a fertilized egg cell can be used.

In the callus formation or embryo-like structure formation step, the obtained substance-introduced fertilized egg cell is cultured to form the embryo-like structure or callus. The step of dividing and inducing fertilized egg cell and allowing the cell to grow so as to form the callus or embryo-like structure is not specifically limited, since the optimal conditions differ depending on plants, but is preferably the nurse culture method with feeder cells added. For example, the procedure can be as follows.

Culture in liquid medium of a fertilized egg cell: Substance-introduced fertilized egg cell is transferred to a medium, followed by standing overnight and culture by gentle shaking. The shaking speed is preferably 30 to 50 rpm, more preferably 35 to 45 rpm. The culture temperature is preferably 24 to 28° C., more preferably 25 to 27° C. The culture is preferably performed in the dark. At this time, feeder cells are preferably added to the medium to perform co-culture (nurse culture method). The culture period is preferably 4 to 14 days, more preferably 5 to 10 days.

Medium: Liquid MS medium (NPL 17), B5 medium (NPL 18), N6 medium (NPL 19), and the like, to which auxins such as 2,4-dichlorophenoxyacetic acid and naphthaleneacetic acid are added.

Auxins such as indole-3-acetic acid, 2,4-D, and dicamba are preferably added to the medium. The concentration of auxins to be added is 0.1 to 3.0 mg/L, for example, preferably 0.1 to 0.3 mg/L, more preferably 0.15 to 0.25 mg/L.

Feeder cells: Any known feeder cells can be used. Examples thereof include a rice cell suspension culture (Line 0c, manufactured by Riken BioResource Research Center), maize nurse cells (NPL 20), and a non-morphogenic cell suspension (NPL 21).

By this step, a spherical embryo-like structure with a diameter of about 50 to 200 μm is formed 4 to 14 days after the start of culture of a fertilized egg cell.

The regeneration step also can be carried out according to a known regeneration step. For example, it can be performed, as follows.

Culture of embryo-like structure: The spherical embryo-like structure is transferred to a medium not containing feeder cells, followed by further culture for about 10 to 14 days. Thereafter, the embryo-like structure is cultured in an arbitrary medium not containing auxins such as the MS medium to form a plant. At this time, the culture is preferably performed under light irradiation, and the light is, for example, preferably 50 to 180 μmol/m$^2$ per second, more preferably 70 to 150 μmol/m$^2$ per second.

Medium: A solid medium such as the MS medium, the B5 medium, and the N6 medium, using agarose, agar, gellan gum, gelrite, or the like, for example, is used.

Substance-Introduced Plant

The present invention further comprises a substance-introduced plant obtained by the method of the present invention. The substance-introduced plant is, for example, a plant into which a substance is transiently or permanently introduced, such as a transformed plant in which introduced nucleic acids are partially or fully integrated into the plant genome, and a plant into which proteins such as nucleic acids and Cas9 nuclease are transiently introduced, so that genome is edited by a genome editing technique. Before the present invention, it has been difficult or impossible to obtain substance-introduced plants, particularly, of "difficult-to-culture" plants and varieties. The present invention enables substance-introduced plants of such plants and varieties to be efficiently obtained by a simple method.

EXAMPLES

Hereinafter, the present invention will be described in detail based on examples, but the present invention is not limited to these examples. Those skilled in the art can easily modify and change the present invention based on the disclosure of this description, and such modifications and changes are included in the technical scope of the present invention.

EXAMPLE 1

Isolation of Maize Fertilized Egg Cell

Pollen collected from the tassel of maize (variety: B73) was conveyed to the stigma of the maize ear in the mating period that had been cultivated in a greenhouse. The mating was performed at about 10:30 a.m. After the mating, the ear was covered with a bag made of paraffin paper, so as to prevent other pollen from flying thereto.

A nucellus slice containing the embryo sac was released from the ovule of the ear 24 hours after the mating and was put into 1 mL of a 10% mannitol solution (650 mosmol/kg H$_2$O) in a 3.5-cm plastic Petri dish. 0.5 mL of an enzyme mixed solution was put into the 3.5-cm plastic Petri dish to give 1.5 mL of an enzyme solution, which was allowed to stand at room temperature for 5 to 45 minutes. The following enzymes were used. Cellulase (manufactured by Worthington Biochemical Corporation), Macerozyme R10 (manufactured by Yakult Honsha Co., Ltd.; polygalacturonase activity: 0.5 unit/mg), Pectolyase Y23 (manufactured by Morishin Pharmaceutical Co., Ltd.; pectin lyase activity: 1 unit/mg), or Sumiteam AP2 (manufactured by SHINNIHON CHEMICALS Corporation; polygalacturonase activity: 12.4 units/mg) was dissolved in a 10% mannitol solution (650 mosmol/kg H$_2$O) to give each concentration shown in Table 1. In each fraction, cellulase was 0.3%. The column of "Pectinases (unit(s)/mL) in enzyme solution" in the tables indicates the total value of the unit(s)/mL of polygalacturonase and pectin lyase.

After performing the treatment for each time shown in Table 1, which will be described below, the enzyme solution was removed with a pipette, and the enzymatically treated nucellus slice was washed twice with a 10% mannitol solution and was put into 1.5 mL of a mannitol solution with the same concentration for isolation operation.

The isolation was performed using two glass needles. The nucellus slice was fixed with one of the glass needles so as not to move, and tissues in the area in which fertilized egg cells are estimated to be present were scraped out with the other glass needle, thereby isolating the fertilized egg cells. When fertilization is carried out, one of the two synergids into which the pollen tube invades degenerates and turns to dark brown colour, and therefore the aforementioned area was estimated using it as a marker. The isolated fertilized egg cells were moved into a droplet on a cover glass using a micro pipette.

The droplet on the cover glass was created by the following method.

1) The periphery of the cover glass is immersed in a 1,1,1-trichloroethane solution containing 5% dichloro methyl silane and then dried;

2) 0.2 to 0.3 mL of mineral oil (Embryo Culture-tested Grade, 1001279270, manufactured by Sigma-Aldrich Corporation) is placed on the center of the cover glass; and to 60 μL of rice cell suspension culture (Line Oc, manufactured by Riken BioResource Research Center) was added to the Petri dish as feeder cells.

Using a washed and sterilized microcapillary, the isolated fertilized egg cells were put into a fresh 10% mannitol solution droplet (650 mosmol/kg $H_2O$) and thereafter were transferred onto a membrane in the CM insert containing the medium for a fertilized cell.

The fertilized egg cells were allowed to stand still at 26° C. in the dark for one day, followed by shaking culture for 20 days.

Table 1 shows the results of the embryo-like structure (embryonic cell mass) formation after the culture. In the sections (test sections 8 to 10) where the enzyme titer, particularly, the unit(s)/mL or the unit(s)/mL multiplied by the time of pectinases is high, the embryo-like structure was not obtained, but in the sections (test sections 1 to 7) in which the unit(s)/mL or the unit(s)/mL multiplied by the time is low, the embryo-like structure could be obtained. However, the growth of the embryo-like structure in test section 7 was slightly poor as compared with the other sections.

TABLE 1

| Test section | Added amount of Pectolyase Y23 (%) | Added amount of Macerozyme R10 (%) | Added amount of Sumiteam AP2 (%) | Pectinases (unit(s)/mL) in enzyme solution | Treatment time (minute(s)) | Unit(s)/mL × time | Possibility of obtaining embryo-like structure |
|---|---|---|---|---|---|---|---|
| 1 | 0.017 | 0.1 | 0 | 0.67 | 5 | 3.3 | + |
| 2 | | | | | 30 | 20.0 | + |
| 3 | | | | | 45 | 30.0 | + |
| 4 | 0.67 | 0 | 0 | 6.67 | 15 | 100.0 | + |
| 5 | | | | | 20 | 133.3 | + |
| 6 | | | | | 30 | 200.0 | + |
| 7 | | | | | 45 | 300.0 | + |
| 8 | 0.17 | 0 | 0.5 | 63.67 | 5 | 318.3 | − |
| 9 | | | | | 10 | 636.7 | − |
| 10 | | | | | 30 | 1910.0 | − |

3) 1 to 2 μL of a 10% mannitol solution (650 mosmol/kg $H_2O$) is inserted into the mineral oil with a micro pipette.

EXAMPLE 2

Obtaining Embryo-Like Structure (Embryonic Cell Mass)

0.2 mL of a medium for a fertilized cell was prepared. The medium for a fertilized cell was N6Z medium (Kumlehn J. et.al. (1998) Planta 205: 327-333) modified with; 2 g/L of CHU (N6) basal salt mixture (manufactured by Sigma-Aldrich Corporation), 0.025 mg/L of $Na_2MoO_4.2H_2O$, 0.025 mg/L of $CoCl_2.6H_2O$, 0.025 mg/L of $CuSO_4.5H_2O$, 0.01 mg/L of retinol, 0.01 mg/L of calciferol, 0.01 mg/L of biotin, 1 mg/L of thiamine.$H_2O$, 1 mg/L of nicotinic acid, 1 mg/L of pyridoxine.HCl, 1 mg/L of choline chloride, 1 mg/L of Ca-pantothenic acid, 0.2 mg/L of riboflavin, 0.2 mg/L of 2,4-D, 0.02 mg/L of cobalamin, 0.02 mg/L of p-aminobenzoic acid, 0.4 mg/L of folic acid, 2 mg/L of ascorbic acid, 40 mg/L of malic acid, 40 mg/L of citric acid, 40 mg/L of fumaric acid, 20 mg/L of Na-pyruvic acid, 1,000 mg/L of glutamine, 250 mg/L of casein hydrolyzate, and 100 mg/L of myoinositol. The osmotic pressure was adjusted to 450 mosmol/kg $H_2O$ (pH5.7) using glucose in the preparation. The medium prepared for a fertilized cell was put into a Millicell CM insert (manufactured by Millipore Corporation) with a diameter of 12 mm, which was put into a 3.5-cm plastic Petri dish containing 2 mL of a medium. Further, 40

EXAMPLE 3

Regeneration of Plant

Figure 6:
FIG. 6 is a plant derived from a fertilized egg cell of maize (B73) regenerated from the embryonic cell mass of FIG. 3 to FIG. 5.

The embryo-like structure (embryonic cell mass) obtained in each of Examples 1 and 2 was transferred to a regeneration medium (modified MS medium; MS salts, MS vitamins, 100 mg/L of myoinositol, 2 g/L of casamino acid, 30 g/L of sucrose, 30 g/L of sorbitol, 0.2 mg/L of l-naphthaleneacetic acid (NAA), 1 mg/L of kinetin, and 0.3% of gelrite). The culture was performed at 30° C. under continuous photoirradiation for 12 to 30 days. As a result, a plant could be obtained (FIG. 6). This result demonstrated that culture from a cell and regeneration to a plant were possible, even in maize B73, which has been considered to be most difficult to culture.

EXAMPLE 4

Introduction of Nucleic Acids into Fertilized Egg

Fertilized eggs were isolated using maize (variety: B73) as a plant material, in the same manner as in Example 1, using enzyme solution of 0.3% of Cellulase (manufactured by Worthington Biochemical Corporation), 0.1% of Macerozyme R10, and 0.017% of Pectolyase Y23, except that the treatment time was changed to 15 minutes. In the enzymatic treatment conditions, the pectinase concentration was 0.67 unit/mL, and the unit(s)/mL multiplied by the treatment time was 10.05.

The isolated fertilized egg cells were moved into a droplet (about 2 µL) of an MMG solution (15 mM of $MgCl_2$, 4 mM of MES (pH5.7), and 10% of mannitol (650 mosmol/kg $H_2O$)) and thereafter were moved into a droplet to which a plasmid (NPL 11) containing a base sequence to be introduced into MMG, 35S promoter::signal sequence::GFP::endoplasmic reticulum retention signal (HDEL)::NOS terminator was added. Next, the droplet containing the fertilized egg cells was mixed with a droplet (about 2 µL) of a PEG solution (7.5 g of PEG4000 and 2.5 mL of a 1M calcium chloride were added to 12.5 mL of a 10% mannitol solution (650 mosmol/kg $H_2O$), and the mixture was adjusted to 25 mL with distilled water), followed by stirring with a glass capillary 30 to 50 times.

The fertilized egg cells into which the nucleic acids had been introduced were transferred to the medium for fertilized cells in the same manner as in Example 3, followed by stationary culture in the dark. After a lapse of 12 to 16 hours from the PEG treatment, the fertilized egg cells were observed with a fluorescent microscope, to check the expression status of the introduced nucleic acids and cell division situation based on the presence or absence of GFP fluorescence.

Figure 7:
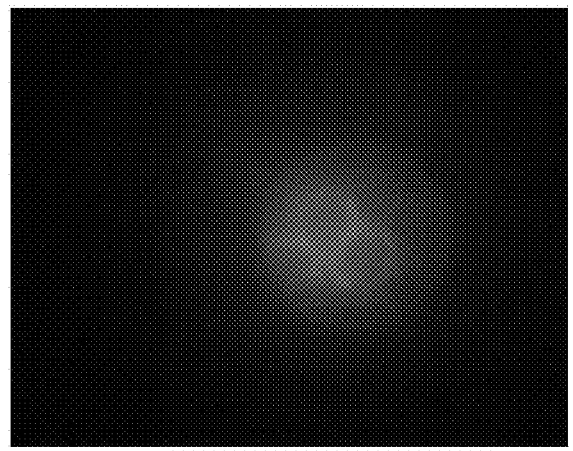
FIG. 7 is a fluorescent microscope image of a fertilized egg cell of maize (B73) that has started to divide after nucleic acids encoding GFP have been introduced by the PEG method.

FIG. 7 shows the results. Since fluorescence of GFP was certainly observed in the fertilized eggs subjected to the treatment to introduce the nucleic acids, it could be confirmed that the nucleic acids had been introduced. Further, start of division could be confirmed.

EXAMPLE 5

Regeneration of Plant from Nucleic Acid-Introduced Fertilized Egg Cell

The embryo-like structure (embryonic cell mass) was obtained according to Examples 2 and 3 from the nucleic acid-introduced fertilized egg cells (maize (variety: B73)) obtained in Example 4, and the embryo-like structure was further cultured. Two weeks thereafter, the medium was updated to a modified N6Z medium free from rice cell suspension culture, followed by further culture for two weeks. The cell mass that had grown to about 2 mm was placed on a caryopsis slice of maize A188 10 days after the mating and was cultured at 25° C. in the light for two days in a regeneration medium containing 5 µM of $CuSO_4.5H_2O$, RMS1 medium (NPL 22). Thereafter, the cell mass was moved to a regeneration medium containing 5 µM of $CuSO_4.5H_2O$, RMS1 medium, and was cultured at 25° C. in the light for two weeks for regeneration.

As a result, multiple individuals were regenerated from the greened cell mass, and thus the cell mass was divided and further cultured at 25° C. in the light in a regeneration medium, RMS2 medium (NPL 22), until rooting. The rooted individuals were sequentially moved to a regeneration medium, RMS3 medium, and were cultured at 25° C. in the light until each shoot grows to about 10 cm. The individuals with reddish brown shoots were cultured in a RMS3 medium containing 10 g/L of ascorbic acid. The individuals that had been sufficiently rooted were transplanted to pots containing soil and were cultivated in a greenhouse. As a result, regenerated individuals could be obtained from one of the fertilized eggs into which the nucleic acids had been introduced.

EXAMPLE 6

Obtaining Rice Egg Cell

An unbloomed flower obtained from the ear of rice was disassembled, to collect the ovary and the anther. The ovary and the anther were put into a 3.5-cm plastic Petri dish containing 3 mL of a 6% mannitol solution (370 mosmol/kg $H_2O$).

The ovary from which the stigma had been removed was submerged into 3 mL of a 6% mannitol solution (370 mosmol/kg $H_2O$) in a new 3.5-cm plastic Petri dish, and the lower part of the ovary was cut at the bottom of the Petri dish using a laser blade (FA-10, manufactured by FEATHER Safety Razor Co., Ltd). Egg cells released from the cut overies were observed by microscopy, and the egg cells were isolated with a microcapillary. About 10 to 15 egg cells were obtained from 30 to 40 ovaries. Each egg cell had a diameter of 40 to 50 µm.

Fertilized eggs are produced by fusing the resultant unfertilized egg cells with isolated sperm cells. Thereafter, the fertilized egg cells are treated with an enzyme solution containing a plant tissue-degrading enzyme under a low-titer condition.

EXAMPLE 7

Introduction of Nucleic Acids into Maize-Derived Fertilized Egg of a Different Variety, and Regeneration of Plant Fertilized eggs of maize variety A188 were isolated in the same manner as in Example 1, except for condition of enzymatic treatment. The enzymatic treatment was performed using an enzyme solution containing 0.33% of cellulase, 0.1% of Macerozyme R10, and 0.017% of Pectolyase Y23 (in the enzyme solution, the pectinase concentration was 4.17 units/mL) for 10 minutes, and further using an enzyme solution containing 0.165% of cellulase, 0.05% of Macerozyme, and 0.008% of pectolyase (in the enzyme solution, the pectinase concentration was 2.08 units/mL) for 20 minutes. The total of the unit(s)/mL multiplied by the treatment time in the enzymatic treatment was 83.4.

A DNA fragment consisting of a base sequence encoding maize ubiquitin promoter::maize ubiquitin intron::GFP::NOS terminator was introduced into the isolated fertilized eggs. Nucleic acids were introduced therein using a MMG solution containing the DNA fragment at a concentration of 150 µg/mL, according to the method of Example 4 using a PEG solution in which the content of PEG4000 was modified to 10 g/25 mL. Thereafter, the fertilized eggs into which the nucleic acids had been introduced were cultured by the method of Example 2. Two weeks thereafter, the medium was updated to a modified N6Z medium free from rice cell suspension culture, followed by further culture for two weeks. The cell mass that had grown to about 2 mm was placed on a caryopsis slice of maize A188 10 days after the mating and was cultured at 25° C. in the light for 6 days in a regeneration medium containing 5 µM of $CuSO_4.5H_2O$, RMS1 medium. Thereafter, the cell mass was moved to a regeneration medium containing 5 µM of $CuSO_4.5H_2O$, RMS1 medium, and was cultured at 25° C. in the dark for two weeks for regeneration. The rooted individuals were sequentially moved to a regeneration medium, RMS3 medium, and were cultured at 25° C. in the light until each shoot grows to about 10 cm. The individuals with reddish brown shoots were cultured in a RMS3 medium containing 10 g/L of ascorbic acid. The individuals that had been sufficiently rooted were transplanted to pots containing soil and were cultivated in a greenhouse. As a result, regenerated individuals could be obtained from the maize A188 fertilized egg into which the nucleic acids had been introduced.

EXAMPLE 8

Introduction of Nucleic Acids into Rice-Derived Fertilized Egg, and Regeneration of Plant Fertilized eggs were isolated from rice (variety: Yukihikari) cultivated in a greenhouse. The fertilized eggs were isolated in the same manner as Example 7 and NPL 11 (Abiko, et al., (2013)) except that the ovary after a lapse of 2 to 3 hours from blooming was collected.

The resultant rice fertilized egg cells were subjected to the enzymatic treatment for 20 minutes in the same manner as in Example 1. However, the enzymatic treatment was performed using an enzyme solution in which each enzyme was dissolved in a 7.5% mannitol solution (450 mosmol/kg $H_2O$) to the concentration of Table 2.

TABLE 2

| Test section | Added amount of cellulases (%) | Added amount of Pectolyase Y23 (%) | Added amount of Macerozyme R10 (%) | Pectinases (unit(s)/mL) in enzyme solution | Treatment time (minute(s)) | Unit(s)/mL × time |
|---|---|---|---|---|---|---|
| 11 | 0.01 | 0.0005 | 0.003 | 0.020 | 20 | 0.40 |
| 12 | 0.013 | 0.0007 | 0.004 | 0.027 | | 0.53 |
| 13 | 0.02 | 0.001 | 0.006 | 0.040 | | 0.80 |

Figure 8:
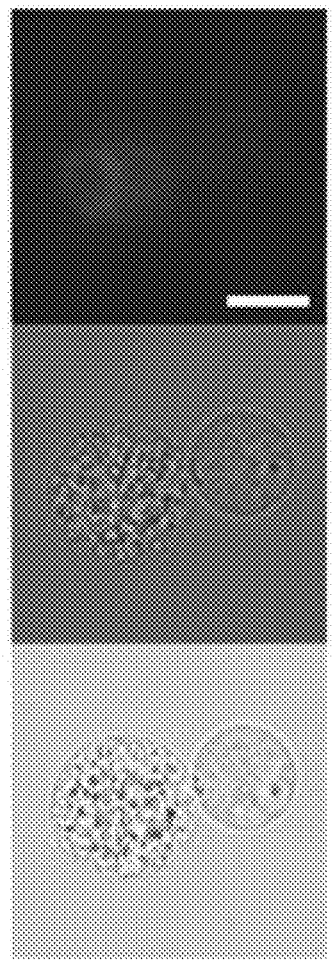
FIG. 8 is a fluorescent microscope image (upper row), an optical micrograph (lower row), and their merge (middle row) of a fertilized egg cell of rice (Yukihikari) that has started to divide after nucleic acids encoding GFP have been introduced by the PEG method. The bar indicates 20 μm.

Into the enzymatically treated rice fertilized eggs, pMON30049 vector containing a DNA fragment consisting of a base sequence encoding 35S promoter::HSP70 intron::SP::GFP::HDEL was introduced. The nucleic acids were introduced using an MMG solution containing the vector at a concentration of 130 μg/mL according to the method of Example 4. Thereafter, 16 to 24 hours after the PEG treatment, the rice fertilized egg cell was observed with a fluorescent microscope, to check the expression of the introduced nucleic acids based on the presence or absence of GFP fluorescence. FIG. 8 shows the results. Further, it could be confirmed that the rice fertilized egg cell had started to divide.

Thereafter, the rice fertilized eggs into which the nucleic acids had been introduced were cultured for 18 to 19 days for regeneration according to NPL 3. As a result, regenerated individuals could be obtained from the rice fertilized eggs into which the nucleic acids had been introduced.

The invention claimed is:

1. A method for introducing a substance into a plant, comprising the steps of:
    obtaining an enzymatically treated and isolated fertilized egg cell by
    (1-i) isolating a fertilized egg cell from a plant tissue containing a fertilized egg cell, and then treating the fertilized egg cell with an enzyme solution containing a plant tissue-degrading enzyme under a low-titer condition,
    (1-ii) treating a plant tissue containing a fertilized egg cell with an enzyme solution containing a plant tissue-degrading enzyme under a low-titer condition, and then isolating the fertilized egg cell that has been enzymatically treated, or
    (1-iii) treating a plant tissue containing a fertilized egg cell with an enzyme solution containing a plant tissue-degrading enzyme under a low-titer condition, and simultaneously isolating the fertilized egg cell that has been enzymatically treated; and
    (2) introducing a substance selected from the group consisting of nucleic acids, proteins, and peptides into the resultant enzymatically treated and isolated fertilized egg cell,
    (3) conducting callus formation or embryo-like structure formation of the fertilized egg cell into which the substance has been introduced; and
    (4) culturing the callused or embryonated tissue in a regeneration medium to obtain a regenerated substance-introduced transformed plant,
    wherein said plant is maize, wheat, barley, rice, or sorghum, and
    wherein
    the enzymatic treatment time is 3-60 minutes, and the plant tissue-degrading enzyme comprises a pectinase, and the unit(s)/mL of the pectinase in the system during the enzymatic treatment of step (1) is at most 60.

2. A method for introducing a substance into a plant, comprising the steps of:
    obtaining an enzymatically treated and isolated fertilized egg cell by
    (1) isolating an egg cell and a sperm cell from a plant, fusing the cells to produce a fertilized egg, and then treating the fertilized egg cell with an enzyme solution containing a plant tissue-degrading enzyme under a low-titer condition,
    (2) introducing a substance selected from the group consisting of nucleic acids, proteins, and peptides into the resultant enzymatically treated and isolated fertilized egg cell,
    (3) conducting callus formation or embryo-like structure formation of the fertilized egg cell into which the substance has been introduced; and
    (4) culturing the callused or embryonated tissue in a regeneration medium to obtain a regenerated substance-introduced transformed plant,
    wherein the plant is maize, wheat, barley, rice, or sorghum, and
    wherein
    the enzymatic treatment time is at least 3-60 minutes, and the plant tissue-degrading enzyme comprises a pectinase, and the unit(s)/mL of the pectinase in the system during the enzymatic treatment of step (1) is at most 60.

3. The method according to claim 1, wherein the plant tissue-degrading enzyme further comprises an enzyme selected from the group consisting of cellulases, proteases, hemicellulases, glucuronidases, zymolyases, chitinases, glucanases, xylanases, galactanases, arabinanases, and lignin-degrading enzymes, and mixtures of two or more of these enzyme groups.

4. The method according to claim 1, comprising isolating an egg cell from a plant tissue containing an egg cell and then fusing the egg cell with a sperm cell to produce a fertilized egg cell.

5. The method according to claim 1, wherein the substance introduction of step (2) is performed within 120 minutes after the enzymatic treatment.

6. The method according to claim 4, wherein the substance introduction of step (2) is performed within 120 minutes after the fusion with a sperm cell.

7. The method according to claim 1, wherein the substance introduction of step (2) is performed using a PEG method or an electroporation method.

8. A method for introducing a substance into a plant, comprising the steps of:
   obtaining an enzymatically treated and isolated fertilized egg cell by
   (1-i) isolating a fertilized egg cell from a plant tissue containing a fertilized egg cell, and then treating the fertilized egg cell with an enzyme solution containing a plant tissue-degrading enzyme under a low-titer condition,
   (1-ii) treating a plant tissue containing a fertilized egg cell with an enzyme solution containing a plant tissue-degrading enzyme under a low-titer condition, and then isolating the fertilized egg cell that has been enzymatically treated, or
   (1-iii) treating a plant tissue containing a fertilized egg cell with an enzyme solution containing a plant tissue-degrading enzyme under a low-titer condition, and simultaneously isolating the fertilized egg cell that has been enzymatically treated;
   (2) introducing a substance selected from the group consisting of nucleic acids, proteins, and peptides into the resultant enzymatically treated and isolated fertilized egg cell;
   (3) conducting callus formation or embryo-like structure formation of the fertilized egg cell into which the substance has been introduced; and
   (4) culturing the callused or embryonated tissue in a regeneration medium to obtain a regenerated substance-introduced transformed plant,
   wherein the plant is maize B73 or a maize variety derived from B73, and
   wherein
   the enzymatic treatment time is 3-60 minutes, and the plant tissue-degrading enzyme comprises a pectinase, and the unit(s)/mL of the pectinase in the system during the enzymatic treatment of step (1) is at most 60.

9. A method for introducing a substance into a plant, comprising the steps of:
   obtaining an enzymatically treated and isolated fertilized egg cell by
   (1) isolating an egg cell and a sperm cell from a plant, fusing the cells to produce a fertilized egg, and then treating the fertilized egg cell with an enzyme solution containing a plant tissue-degrading enzyme under a low-titer condition;
   (2) introducing a substance selected from the group consisting of nucleic acids, proteins, and peptides into the resultant enzymatically treated and isolated fertilized egg cell;
   (3) conducting callus formation or embryo-like structure formation of the fertilized egg cell into which the substance has been introduced; and
   (4) culturing the callused or embryonated tissue in a regeneration medium to obtain a regenerated substance-introduced transformed plant,
   wherein the plant is maize B73 or a maize variety derived from B73, and
   wherein
   the enzymatic treatment time is 3-60 minutes, and the plant tissue-degrading enzyme comprises a pectinase, and the unit(s)/mL of the pectinase in the system during the enzymatic treatment of step (1) is at most 60.

10. The method of claim 1 wherein the plant tissue-degrading enzyme comprises a pectinase, and the unit(s)/mL of the pectinase in the system during the enzymatic treatment of step (1) multiplied by the treatment time (minutes) is at most 200.

11. The method of claim 2 wherein the plant tissue-degrading enzyme comprises a pectinase, and the unit(s)/mL of the pectinase in the system during the enzymatic treatment of step (1) multiplied by the treatment time (minutes) is at most 200.

12. The method of claim 8 wherein the plant tissue-degrading enzyme comprises a pectinase, and the unit(s)/mL of the pectinase in the system during the enzymatic treatment of step (1) multiplied by the treatment time (minutes) is at most 200.

13. The method of claim 9 wherein the plant tissue-degrading enzyme comprises a pectinase, and the unit(s)/mL of the pectinase in the system during the enzymatic treatment of step (1) multiplied by the treatment time (minutes) is at most 200.

* * * * *